United States Patent [19]

Adler-Golden et al.

[11] Patent Number: 4,723,438

[45] Date of Patent: Feb. 9, 1988

[54] SPARK SPECTROSCOPIC HIGH-PRESSURE GAS ANALYZER

[75] Inventors: Steven Adler-Golden, Newtonville; Lawrence S. Bernstein, Bedford; Fritz Bien, Concord, all of Mass.

[73] Assignee: Spectral Sciences, Inc., Burlington, Mass.

[21] Appl. No.: 810,609

[22] Filed: Dec. 19, 1985

[51] Int. Cl.⁴ .............................................. G01J 3/30
[52] U.S. Cl. ....................................... 73/23; 356/313
[58] Field of Search ................. 73/23, 29; 356/313; 324/403

[56] References Cited

U.S. PATENT DOCUMENTS 3,627,421 12/1971 Harley et al. ............... 356/313
3,876,306 4/1975 Onodera et al. ............. 356/313
4,255,051 3/1981 Imamura et al. ............ 356/313

Primary Examiner—Stewart J. Levy
Assistant Examiner—Joseph W. Roskos
Attorney, Agent, or Firm—Joseph S. Iandiorio; William E. Noonan

[57] ABSTRACT

A spark spectroscopic high-pressure gas analyzer including a spark chamber, having a pair of electrodes, for receiving a sample of the pressurized gas to be analyzed. A voltage is provided across the electrodes for generating a spark in the pressurized gas sample. A selected wavelength band of radiation emitted from the spark discharge in the pressurized gas corresponding to a component to be sensed in the gas is detected. The intensity of the emission in the wavelength band is integrated during the afterglow time interval of the spark emission and a signal representative of the integrated intensity of the emission in the selected narrow wavelength band is employed to determine the proportion of the component in the gas.

36 Claims, 10 Drawing Figures

SPARK SPECTROSCOPIC HIGH-PRESSURE GAS ANALYZER

FIELD OF INVENTION

This invention relates to a spark spectroscopic high-pressure gas analyzer and more particularly to a device which detects the presence and amount of a component in a pressurized gas sample by detecting a selected narrow wavelength radiation band which is emitted from a spark discharge in the pressurized gas and which corresponds to the component to be detected.

BACKGROUND OF INVENTION

In conventional techniques for analyzing the composition of gas streams a gas sample is typically placed in an instrument such as a gas chromatograph or an optical or mass spectrometer which is outside of the stream. However, these instruments do not permit sensitive in-stream, real-time detection and analysis of gas samples. For example, it is very desirable to monitor the water content in the high-pressure helium coolant of a high-temperature gas reactor. Presently, this is accomplished by passing the helium sample over a cooled mirror which condenses the water. The presence of condensation is indicated by a change in reflection of a beam of light directed at the mirror. This technique exhibits a number of disadvantages, such as a long response time and complex instrument design. Further, it is often desirable to measure the presence and amount of numerous other trace elements and compounds, for example carbon, oxygen, sulfur, nitrogen, phosphorus, chlorine and fluorine, in high-pressure gas samples to which the mirror-condensation approach is not suited.

Trace element detection can be successfully performed at atmospheric and subatmospheric pressures using emission spectra obtained from microwave and direct current discharges. However, these techniques are not suitable for use in high pressure gas samples such as are found in the high temperature gas reactor.

SUMMARY OF INVENTION

It is therefore an object of this invention to provide a spark spectroscopic high-pressure gas analyzer which accurately detects the presence and amount of a trace component in a high-pressure gas sample.

It is a further object of this invention to provide a spark spectroscopic high-pressure gas analyzer which provide enhanced sensitivity and a faster response time than prior devices.

It is a further object of this invention to provide a spark spectroscopic high-pressure gas analyzer which uses a signal generated by emission spectra remaining during the afterglow time interval following spark discharge to identify the presence and amount of a trace component in a high-pressure gas sample.

It is a further object of this invention to provide a spark spectroscopic high-pressure gas analyzer which effectively compensates for drift and erroneous signals.

It is a further object of this invention to provide a spark spectroscopic high-pressure gas analyzer which is particularly effective for detecting and measuring water present in a high-pressure helium cooling system of a nuclear reactor.

This invention results from the realization that spark spectroscopic detection of trace components in a sample gas may be improved considerably by measuring the intensity of the emission spectra resulting from the spark discharge during the "afterglow" period, e.g. the time interval which follows subsiding of the intense continuous background signal across the entire spectrum caused by the spark discharge. This invention results from the further realization that such detection can be improved even further by compensating the measured intensity for variations not resulting from variation in the proportion of the target component, e.g. variations caused by fluctuations in the intensity of the successive spark discharges.

This invention features a spark spectroscopic high-pressure gas analyzer which has a spark chamber including a pair of electrodes for receiving a sample of pressurized gas to be analyzed and means for providing a voltage across the electrodes for generating a spark in the pressurized gas sample. There are means for detecting a first selected narrow wavelength band of radiation emitted from the spark discharge in the pressurized gas corresponding to a component to be detected in the gas. There are means for integrating, during the afterglow time interval of the spark emission, the intensity of the emission in the first wavelength band and means responsive to a signal representative of the integrated intensity of the emission in the selected narrow wavelength band for determining the proportion of the component in the gas.

In a preferred embodiment the gas to be analyzed has a pressure of one atmosphere but no greater than 100 atmospheres and that pressure may be at least 10 atmospheres. The gas to be analyzed may include helium and the component to be detected may be water. The electrodes may be spaced between 1 mm. and 3 mm. apart and a voltage of up to 50 kilovolts may be applied across the electrodes.

The narrow band selected may include the wavelength 6563 Angstroms. The means for detecting may include a monochromator, or alternatively an interference filter, for selecting the narrow wavelength band. The means for determining may include a microprocessor and more specifically may include means for calculating the proportion of the component in the gas and/or means for retrieving a stored predetermined proportion of the component in the gas corresponding to a signal representative of the intensity of the emission in the first band.

Further included may be means for compensating the intensity of the radiation emitted in the first narrow wavelength band for variations not due to variations in the proportion of the component being tested in the gas. Such means for compensating typically includes means for averaging a signal representative of the intensity of the emission in the first band over a plurality of spark discharge cycles. The means for integrating and means for averaging may include a boxcar averager.

The means for compensating may further include means for detecting the radiation emitted from the spark discharge in the pressurized gas in a second selected narrow wavelength band which does not correspond to the component to be detected in the gas and means for combining a signal representative of the intensity of the emission in the first band and a signal representative of the intensity of the emission in the second band. Means may be provided for integrating, during the afterglow time interval of the spark emission, the intensity of the radiation in the second selected band. First means, responsive to the means for integrating the intensity of emission in the first band may be provided for averaging over a plurality of spark discharge cycles the integrated intensity of emission in the first band and second means, responsive to the means for integrating the intensity of emission in the second band, may be provided for averaging over a plurality of spark discharge cycles the integrated intensity of emission in the second band. The means for integrating and averaging in the first band and/or the means for integrating and averaging in the second band may include respective boxcar averagers. In such an embodiment, the means for combining may include means for comparing the averaged integrated intensity of the emitted radiation in the first band and the averaged integrated signal intensity of the emitted radiation in the second band and for providing to the means for determining an output representative of the averaged integrated intensity of emission in the first band.

Alternatively, the means for combining may include means for comparing the integrated intensity of the emission in the first band and the integrated intensity of the emission in the second band. Means, responsive to such means for comparing, may be provided for averaging over a plurality of spark discharge cycles the output from the means for comparing and providing that output to the means for determining. Means, responsive to such means for comparing may be provided for averaging over a plurality of spark discharge cycles the output from the means for comparing and providing an averaged output to the means for determining.

Means may be provided for sensing the pressure of the gas to be analyzed. The means for determining may be further responsive to such means for sensing the pressure for determining the proportion of the component in the gas at the sensed pressure. Means may be provided for sensing the temperature of the gas to be analyzed and in such embodiments the means for determining is further responsive to the means for sensing the temperature for determining the proportion of the component in the gas at the sensed temperature. The means for determining may include means for resolving the water concentration (e.g., the absolute humidity) and/or relative humidity of the gas.

Conduit means may be provided for conducting radiation emitted by the spark discharge from the source to the means for detecting and such conduit means may include fiber optics.

Means responsive to the means for determining may be provided for indicating the proportion of the component in the gas. Such means may include alarm means for indicating the presence of at least a predetermined proportion of the component in the gas.

DESCRIPTION OF PREFERRED EMBODIMENT

Other objects, features and advantages will occur from the following description of a preferred embodiment and the accompanying drawings, in which.

Figure 1:
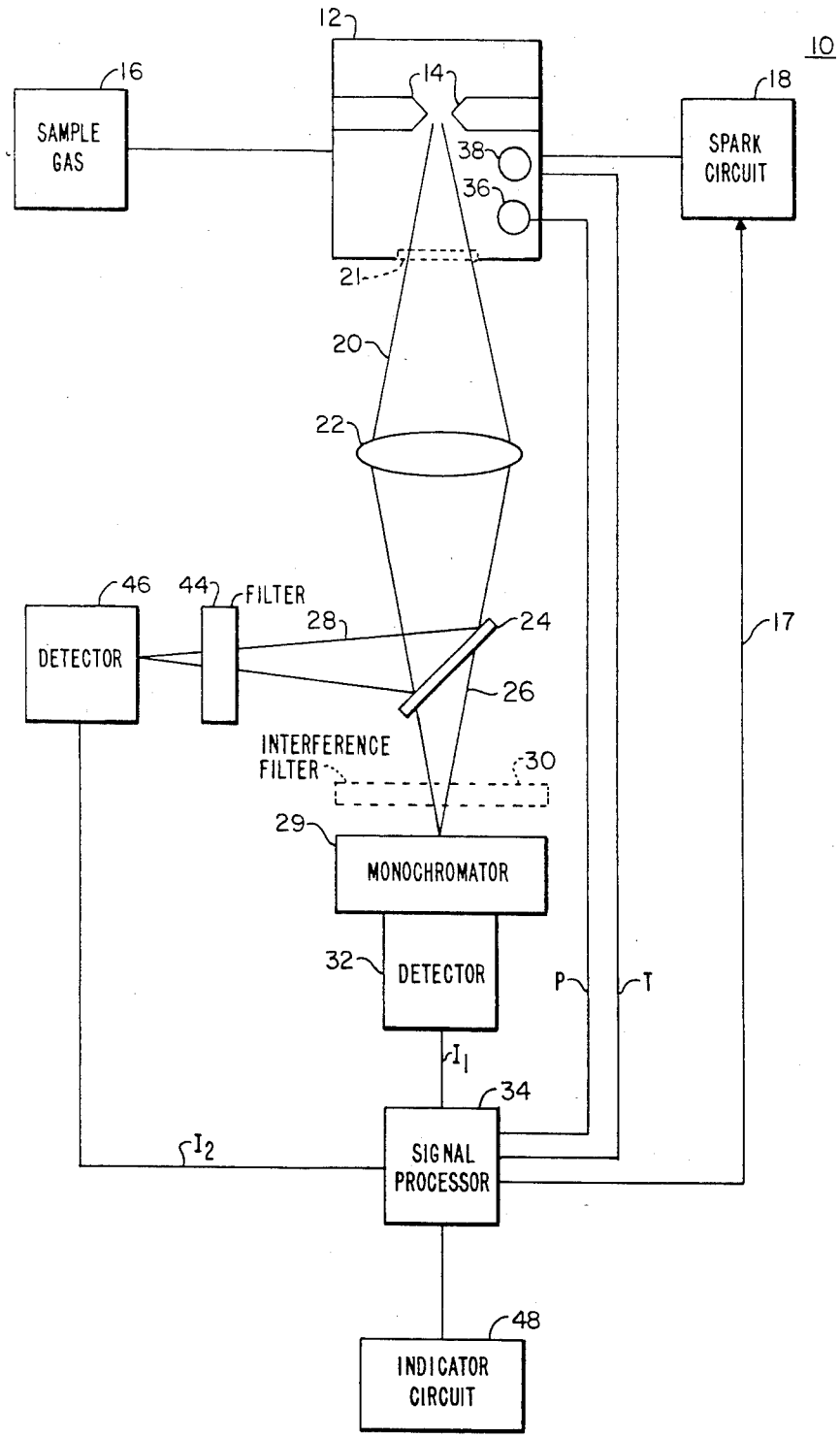
FIG. 1 is a schematic diagram of a spark spectroscopic high-pressure gas analyzer according to this invention.

A spark spectroscopic high-pressure gas analyzer according to this invention may be accomplished using a spark chamber for receiving pressurized gas to be analyzed. Various gas samples may be analyzed for a variety of atomic components such as carbon, oxygen, sulfur, nitrogen, phosphorus, arsenic, fluorine, chlorine, or bromine. The device is particularly beneficial for the detection of water in high-pressure helium, such as is employed in the cooling systems of nuclear reactors. Typically, the gas is provided at a pressure above one atmosphere but no greater than 100 atmospheres. The reactor helium coolant is typically provided at a pressure of approximately 50 atmospheres.

The spark chamber includes a pair of electrodes preferably spaced between 1 mm. and 3 mm. apart. A transformer may be employed to provide a stepped-up voltage of up to 50 Kv, for example, 35 Kv, which is applied across the electrodes to generate a spark in the pressurized gas sample. The spark typically has a duration on the order of tenths of a microsecond. The spark pulses are provided repetitively at a frequency of typically 1–10 Hz. Each spark causes the component being monitored in the pressurized gas sample to emit a characteristic spectrum. The emitted radiation typically has a lifetime on the order of several microseconds.

Means such as a monochromator or an interference filter are provided for detecting a first selected narrow wavelength band of the emitted radiation. When water is the component to be detected, the narrow wavelength band selected typically includes the wavelength 6563 Angstroms which is an emission line for hydrogen (H). Detector means, including a photomultiplier or photodetector, are provided for sensing the first narrow wavelength band selected by the monochromator or interference filter.

To maintain consistent intensity measurements means may be provided for normalizing or otherwise compensating the intensity of the radiation emitted in the first band to correct for errors resulting, for example, from fluctuations in spark intensity, over successive discharges. To perform such compensation, means are provided for averaging a signal representative of the intensity of the emission spectra in the first band over a plurality of spark discharge cycles. Such means for averaging may be combined with the means for integrating in a boxcar averager. Alternatively, an entirely distinct pulse averager may be used. Erroneous signals may also be compensated using a second optical band. To accomplish this, radiation emitted from the spark discharge in a second selected narrow wavelength band, e.g., 6580 Angstroms, which does not correspond to the component being sensed is also detected. Respective intensity signals representative of the radiation emitted in the first and second bands are then integrated during the afterglow time interval of the spark emission (e.g., starting 1 or 2 microseconds after the spark discharge). The integrated signal from the second band is compared or combined with that of the first band through division, subtraction or otherwise to provide a compensated signal representative of the intensity of the emission in the first band. This signal, which is pulsed, is then averaged over many sparks such as by a low pass filter. Alternatively, each of the intensity signals are integrated and averaged in respective boxcar averagers which provide signals representative of the intensities in the first and second bands to a comparator, where they are combined.

In either case a compensated signal representative of the intensity of the emission in the first narrow wavelength band is provided to a microprocessor or other means for determining the proportion of the component in the gas. The means for determining may include retrieval means for retrieving a stored predetermined proportion of the component in the gas corresponding to the signal representative of the intensity of the emission in the first band. Alternatively, means may be provided for calculating the proportion of the component in the gas. The means for determining may be temperature and/or pressure dependent. An oscilloscope, computer readout or other means may be provided for indicating the intensity of the emission in the first band and therefore the proportion of the component in the gas. An audio or visual alarm may also be provided for indicating the presence of at least a predetermined proportion of the component in the gas. Such a feature is particularly important for the monitoring of water in the reactor coolant and for the detection of toxic gases. When water is the subject component, circuitry may also be provided for resolving the water concentration, the absolute humidity and/or the relative humidity of the gas sample.

In certain embodiments, fiber optics or other conduit means may be provided for conducting the radiation emitted by the spark discharge from the source to the means for detecting.

There is shown in FIG. 1 a spark spectroscopic high-pressure gas analyzer 10 including a spark chamber 12 having electrodes 14. Sample gas 16, such as helium with a pressure of up to 100 atmospheres, for example 50 atmospheres, is introduced into chamber 12. In response to timed signals over line 17 from signal processor 34, spark circuit 18 applies a voltage across electrodes 14 to generate sparks in chamber 12. This creates a plasma which emits intense continuous background radiation. The radiation emitted by the high-pressure helium gas designated as radiation 20, passes through window 21 in chamber 12 and is directed by lens 22 to a beam splitter 24. A portion 26 of the radiation passes through and a second portion 28 is reflected from beam splitter 24. A monochromator 29 transmits only radiation in a first selected wavelength band which corresponds to the component to be detected in the gas sample. When the component to be detected is water, the selected wavelength band is typically centered about the emission line for hydrogen (H) at 6563 Angstroms. All other wavelengths are blocked by monochromator 29. Alternatively, this filtering may be performed by an interference filter 30.

The radiation in the first selected band is sensed by detector 32 and a signal $I_1$ representative of the intensity of the detected radiation is provided to signal processor 34 which determines the proportion of the component in the gas sample. Pressure in the gas sample is monitored by pressure monitor 36 and temperature is sensed by monitor 38 and respective signals P and T representative of those conditions are provided to signal processor 34.

To compensate for variations in the spark intensity over successive spark emissions the reflected radiation portion 28 is directed to a filter 44 which may include either a monochromator or interference filter as previously described. Filter 44 transmits only radiation in a second narrow band not corresponding to the component (e.g., water) to be detected in the gas. That second band of radiation is detected by detector 46 which provides to signal processor 34 a signal $I_2$ representative of the intensity of that detected radiation. A compensated signal representative of the intensity of the radiation emitted in the first band is processed in processor 34 to determine the proportion of the subject component in the sample gas. That proportion is indicated by indicator 48.

Figure 2:
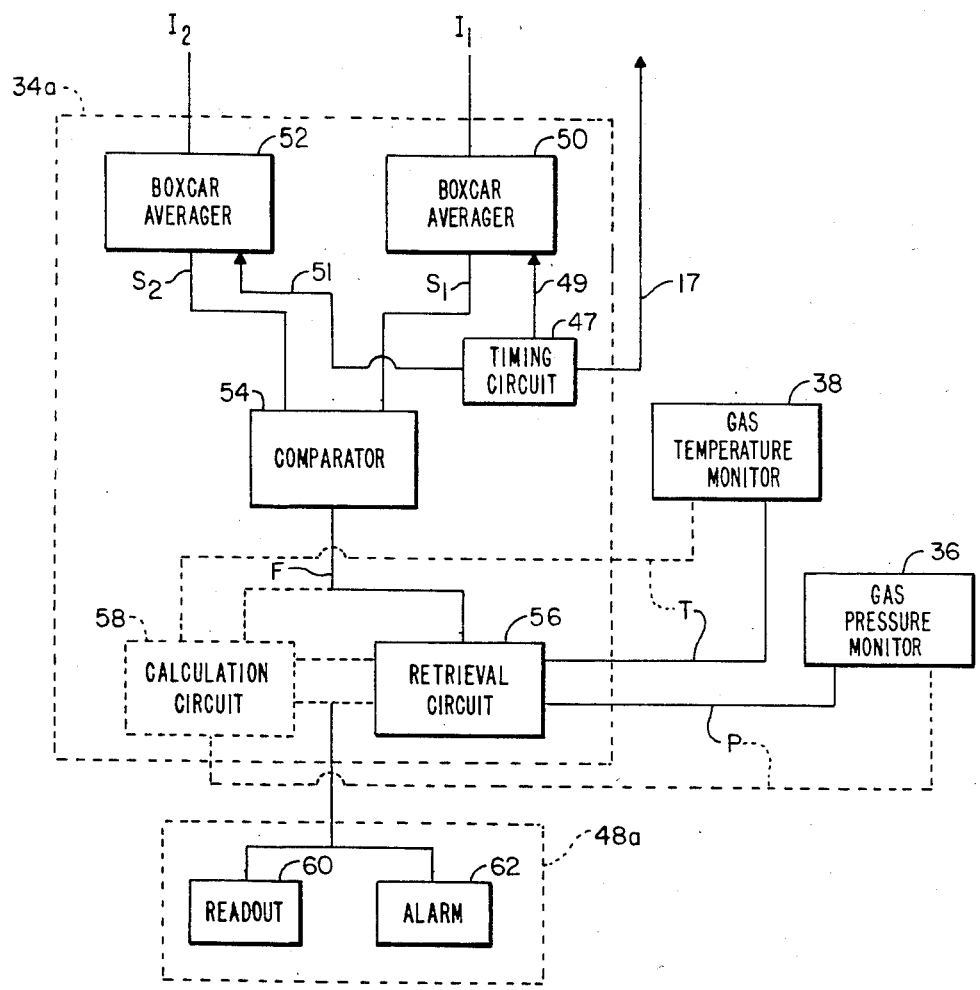
FIG. 2 is a detailed schematic diagram of the indicator circuit and signal processor of FIG. 1.
Figure 3:
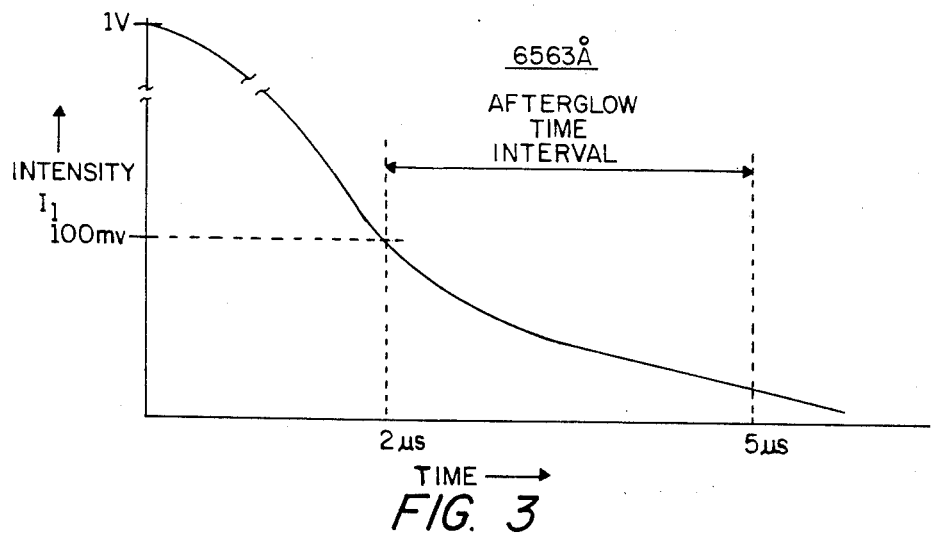
FIG. 3 is a curve illustrating variation in the intensity over time of the emitted radiation in a selected wavelength band corresponding to the component being detected.

An acceptable signal processor 34a for processing signals $I_1$ and $I_2$ is shown in FIG. 2. Signals $I_1$ and $I_2$ are delivered to respective boxcar averagers 50 and 52. As shown in FIG. 3, the intensity of signal $I_1$ immediately after each spark initiation is approximately 1 volt. At that time the signal is due mainly to the background intensity of the spark plasma. The signal strength subsequently drops to approximately 100 millivolts at the beginning of the afterglow time interval (e.g., at about 2 microseconds following spark initiation). During the afterglow period of approximately 2-5 microseconds following discharge, the background intensity has subsided sufficiently so that the emission spectra of the component being measured are evident and distinguishable from the background radiation.

Timing circuit 47, FIG. 2, which provides signals at predetermined times over line 17 to activate spark circuit 10, FIG. 1, also provides a timed signal at the beginning of the afterglow period, e.g. two microseconds, over line 49 to boxcar averager 50. This causes boxcar averager 50 to integrate the intensity of signal $I_1$ during the afterglow period. At the end of the afterglow period, timing circuit 47 instructs boxcar averager 50 to stop integration. Boxcar averager 50 averages a number of successive integrated intensity signals to compensate for variations in the intensity of the spark itself over successive discharges. It then provides a signal $S_1$, which is representative of (e.g., a function of) the pulse-averaged intensity of the emission in the first wavelength band.

Figure 4:
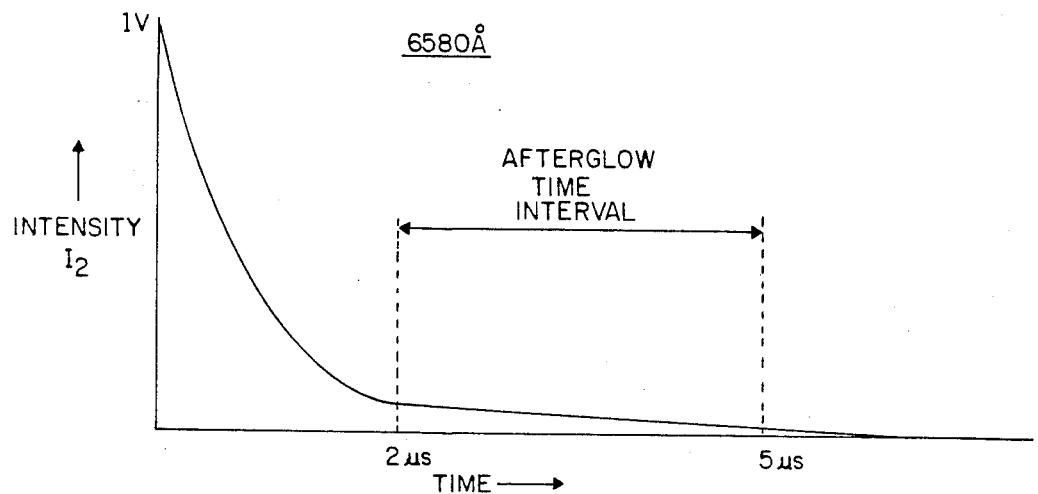
FIG. 4 is a curve illustrating variation in the intensity over time of the emitted radiation in a second narrow wavelength band not corresponding to the component being detected.

The time evolution of signal $I_2$ including a wavelength of 6580 Angstroms is shown in FIG. 4. Because the characteristic emission line which corresponds to the subject component is absent, the intensity in the second band drops off rapidly. At two microseconds after discharge, timing circuit 47 provides a signal over line 51 to a second boxcar averager 52, which is operated during the afterglow time interval to integrate signal $I_2$. The integrated intensity signal is then averaged by boxcar averager 52 to yield a signal $S_2$. Those skilled in the art will recognize that instead of a single distinct timing circuit, separate timing circuits may be provided integrally with each of the boxcar averagers.

Signals $S_1$ and $S_2$, FIG. 2, are delivered to a comparator 54 where they are divided, subtracted or otherwise combined or compared to provide a signal F which is representative of the integrated intensity of the radiation in the first band compensated for variations, e.g. false readings, caused by, for example, contaminants, dirty optics, or variations in background radiation. That signal is provided to a retrieval circuit 56 where the proportion of the water or other component in the sample is retrieved from calibration curves stored in the memory of the circuit. Alternatively, the proportion of water in the gas sample may be determined by entering signal F into a calculation circuit 58. In either embodiment gas pressure sensor 36 monitors the pressure in the sample and temperature monitor 38 senses the temperature of the sample. Retrieval circuit 56 or calculation circuit 58 respond to the gas pressure and temperature measurements to determine the proportion of the water in the helium at the sensed pressure and temperature. The determined water proportion is indicated on a readout 60 in indicator circuit 48a. If the proportion reaches an undesirably high level an alarm 62 is activated.

Figure 5:
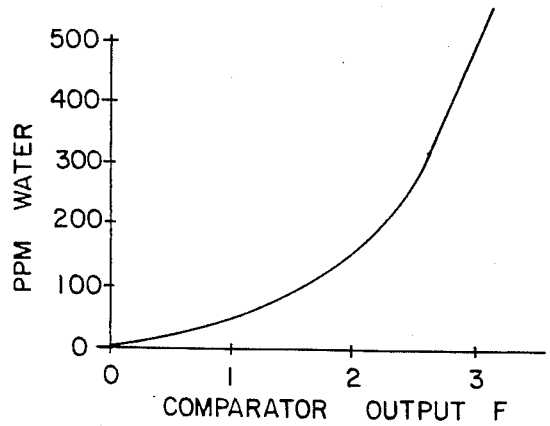
FIG. 5 is a curve illustrating the comparator output F versus the proportion of water in a helium sample.

A curve which may be used by circuit 56 for determining stored water proportion values for a sample of high pressure helium is shown in FIG. 5. Values along the x axis represent the normalized signal F provided to the retrieval circuit. Values along the y axis indicate the proportion of water in the helium in parts per million. This calibrated curve is compiled by employing gas samples having known water proportions and predetermined temperatures and pressures and measuring the values F for such samples.

Figure 6A:
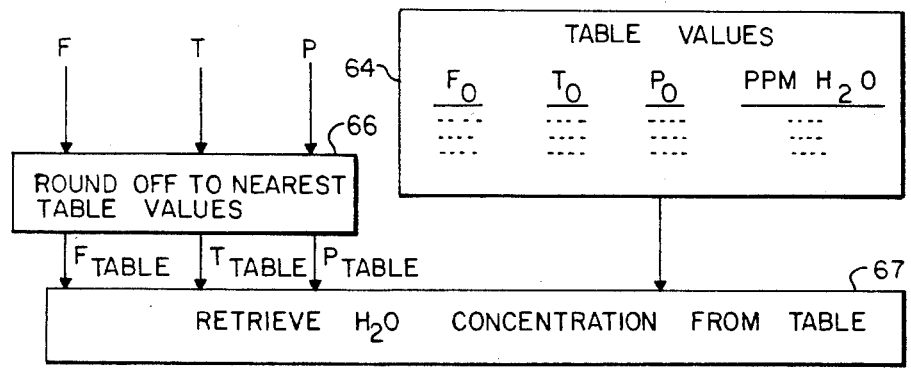
FIG. 6A is a flow chart for retrieving from a table the proportion of water in a gas sample.
Figure 6B:
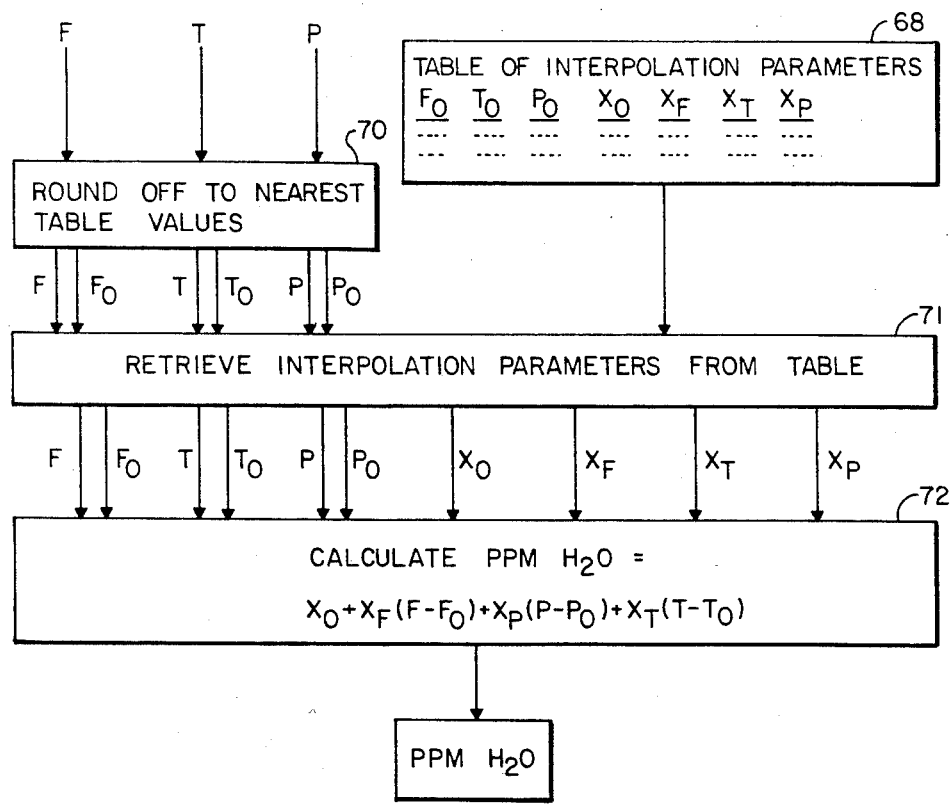
FIG. 6B is a flow chart for interpolating the proportion of water in the gas sample.

Logic which may be used to resolve the proportion of water in a gas sample are shown in FIGS. 6A and 6B. In FIG. 6A predetermined values of signal $F_o$, temperature $T_o$ and pressure $P_o$ and corresponding values of water concentration (ppm H$_2$O) are provided in a table 64. The measured values F, T, and P are rounded off to their nearest table values $F_o$, $T_o$ and $P_o$, and the water concentration corresponding to the three values is retrieved, 67, from table 64.

Alternatively, interpolation may be employed as shown in FIG. 6B. Table 68 includes various known values for the integrated comparison signal $F_o$, the temperature $T_o$ and pressure $P_o$ as well as corresponding values of water concentration $X_o$ and interpolation parameters $X_F$, $X_T$ and $X_P$ for the $F_o$, $T_o$ and $P_o$ values. The measured values F, T and P are rounded off, 70, and paired with corresponding table values $F_o$, $T_o$ and $P_o$. The corresponding values in table 68 are retrieved 71 to acquire the appropriate water concentration $X_o$ and interpolation parameters $X_F$, $X_T$ and $X_P$ for $X_o$, $T_o$ and $P_o$. Water concentration for the measured sample is then resolved by interpolation and in particular by calculating 72 the expression:

$$X_o + X_F(F - F_o) + X_P(P - P_o) + X_T(T - T_o).$$

Figure 7:
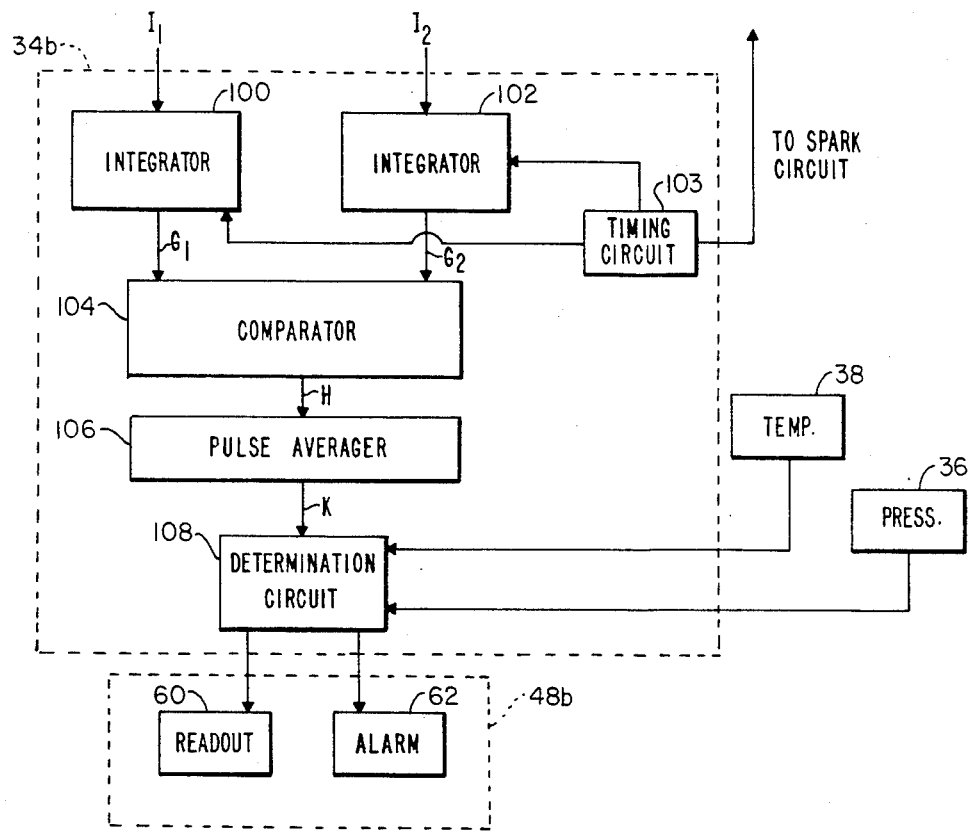
FIG. 7 is a schematic diagram of an alternative signal processor according to this invention.

In a preferred embodiment, FIG. 7, signal processor 34b includes a pair of integrators 100, 102, operated at timed intervals by timing circuit 103 to integrate the respective intensity signals $I_1$ and $I_2$ during the afterglow time interval and provide integrated signals $G_1$ and $G_2$ to comparator 104. There the signals are compared by dividing or subtracting them or otherwise processing them to provide a compensated signal which is representative of the compensated intensity of the radiation in the first band. Pulsed signal H is averaged over many sparks in pulse averager 106 which may be a low pass filter and which provides a smoothed signal K to a determination circuit 108. Circuit 108 typically includes either a retrieval or calculation circuit as previously described which responds to the integrated, averaged, compensated signal as well as to pressure and temperature signals from pressure sensor 36 and temperature sensor 38 for resolving the water concentration, e.g., the absolute humidity. Readout 60 and alarm 62 of indicator circuit 48b again provide appropriate indications of the proportion of water in the sample.

Figure 8:
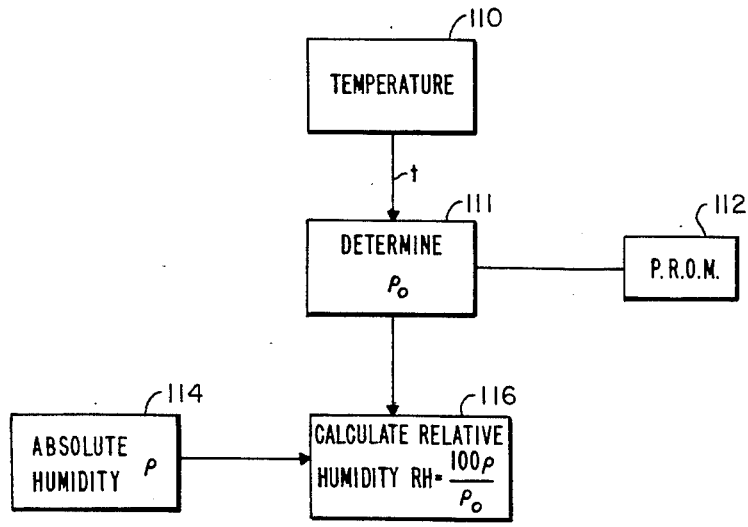
FIG. 8 is a flow chart for resolving the relative humidity of a gas sample.

Relative humidity is determined from the absolute humidity as shown in FIG. 8. First, temperature t is obtained, 110. The saturation density $\rho_o$ for that temperature is then obtained, 111, from a programmable read only memory 112. Absolute humidity $\rho$ (e.g., water concentration) has been derived as previously described and the relative humidity RH is provided by solving 116 for RH = 100 $\rho/\rho_o'$.

In operation, gas 16 is introduced into chamber 12. Timing circuit 103, FIG. 7, sends signals at predetermined intervals over line 17 to spark circuit 18 which cause sparks to be generated across electrodes 14 and radiation 20 to be emitted from chamber 12. Radiation 20 is directed by lens 22 to beam splitter 24, which transmits a portion 26 of the beam and reflects a second portion 28. Monochromator 29 transmits only a wavelength band of beam portion 26 which is emitted by the component being monitored in the gas sample. Detector 32 measures the intensity of this band and provides a signal $I_1$ to signal processor 34b. Detector 46 measures the intensity of a wavelength band of beam portion 28 which is not emitted by the test component upon spark discharge and provides a second intensity signal $I_2$ to signal processor 34b. Timing circuit 103 instructs integrators 100, 102 to integrate respective signals $I_1$, $I_2$ during the afterglow period and integrated signals $G_1$, $G_2$ are then divided, subtracted or otherwise combined in a comparator 104 to compensate for any intensity variation, e.g. erroneous signals, not due to variations in the proportion of the test component. Additional errors are compensated for by averaging the compared integrated intensity signal H in low pass filter 106. An averaged signal K is then provided to determination circuit 108 where the intensity dependent signal K and temperature and pressure measurements are employed, as previously described, to retrieve or calculate the proportion of the test component present in the gas sample. Where water is the target component, humidity may be determined as indicated above. Appropriate signals are then provided to readout 60 and alarm 62 of indicator circuit 48b.

Figure 9:
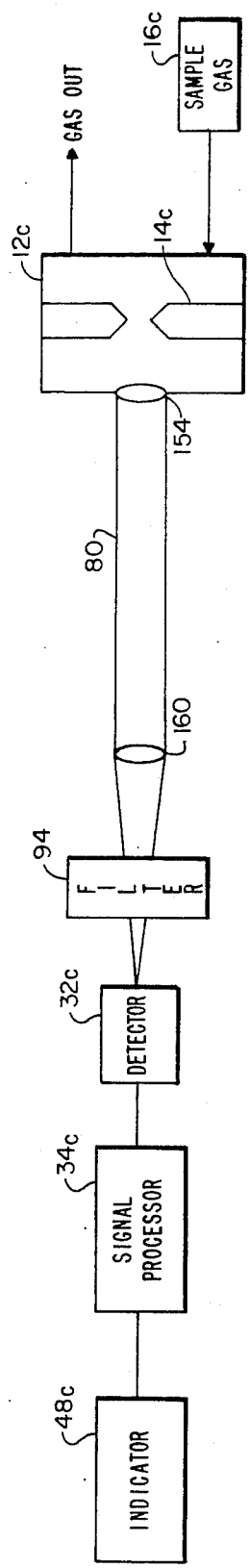
FIG. 9 is a schematic diagram of a gas analyzer of this invention using fiber optics to conduct light to the detector.

A conduit such as optical fiber 80, FIG. 9, may be connected between spark chamber 12c and detector 32c. Such fiber optics may also be employed for conducting the compensating beam of radiation, e.g., portion 28, FIG. 1. Radiation emitted by the sample gas in chamber 12c in response to a spark generated across electrodes 14c is collected by lens 154 and transmitted through fiber 80, lens 160, and filter 94, which transmits only radiation in a narrow wavelength band corresponding to the component in the gas to be detected. The intensity of that narrow band is detected by detector 32c. Signal processor 34c processes the intensity signal as previously described to determine the proportion of the component present in the sample gas. That proportion is shown by indicator 48c.

Although specific features of the invention are shown in some drawings and not in others, this is for convenience only as each feature may be combined with any or all of the other features in accordance with the invention. Other embodiments will occur to those skilled in the art and are within the following claims:

What is claimed is:

1. A spark spectroscopic high-pressure gas analyzer comprising:
   a spark chamber including a pair of electrodes for receiving a sample of pressurized gas to be analyzed;
   means for providing a voltage across said electrodes for generating a spark in said pressurized gas sample;
   means for detecting a first selected narrow wavelength band of the radiation emitted from the spark discharge in said pressurized gas corresponding to a component to be detected in the gas;
   means for integrating the intensity of the emission in the first wavelength band;
   control means for enabling said means for providing and for subsequently enabling said means for integrating during the afterglow time interval of the spark emission; and
   means responsive to a signal representative of the integrated intensity of the emission in the selected narrow wavelength band for determining the proportion of the component in the gas.

2. The gas analyzer of claim 1 further including conduit means for conducting radiation emitted by said spark discharge from said source to said means for detecting.

3. The gas analyzer of claim 2 in which said conduit means includes fiber optics.

4. The gas analyzer of claim 1 in which said means for determining includes means for calculating the proportion of the component in the gas.

5. The gas analyzer of claim 1 in which said means for detecting includes an interference filter for selecting said narrow wavelength band.

6. The gas analyzer of claim 1 further including means responsive to said means for determining for indicating the proportion of the component in the gas.

7. The gas analyzer of claim 1 further including alarm means responsive to said means for determining for indicating the presence of at least a predetermined proportion of the component in the gas.

8. The gas analyzer of claim 1 in which said means for determining includes means for resolving the water concentration in the gas.

9. The gas analyzer of claim 1 in which said means for determining includes means for resolving the relative humidity of the gas.

10. The gas analyzer of claim 1 in which said gas to be analyzed has a pressure above one atmosphere but no greater than one hundred atmospheres.

11. The gas analyzer of claim 1 in which said gas to be analyzed has a pressure of at least ten atmospheres.

12. The gas analyzer of claim 1 in which said gas to be analyzed includes helium.

13. The gas analyzer of claim 1 in which the component to be detected is water.

14. The gas analyzer of claim 1 in which said electrodes are spaced between 1 mm and 3 mm apart.

15. The gas analyzer of claim 1 in which the voltage applied across said electrodes is not more than fifty kilovolts.

16. The gas analyzer of claim 1 in which the first narrow band selected includes the wavelength 6563 Angstroms.

17. The gas analyzer of claim 1 in which said means for determining includes a microprocessor.

18. The gas analyzer of claim 1 in which said control means includes means for determining the beginning of said afterglow time interval.

19. The gas analyzer of claim 18 in which said means for determining includes timing means for establishing a preselected time period between spark generation and the beginning of said afterglow time interval.

20. The gas analyzer of claim 18 in which said means for determining further determines the end of said afterglow time interval.

21. A spark spectroscopic high-pressure helium analyzer comprising:
   a spark chamber including a pair of electrodes for receiving a sample of pressurized helium to be analyzed;
   means for providing a voltage across said elecctrodes for generating a spark in said pressurized helium sample;
   means for detecting a selected narrow wavelength band of the radiation emitted from the spark discharge in said pressurized helium corresponding to water to be detected in the helium;
   means for integrating the intensity of the emission in the selected narrow wavelength band;
   control means for enabling said means for providing and for subsequently enabling said means for integrating during the afterglow time interval of the spark emission; and
   means responsive to a signal representative of the integrated intensity of the emission in the selected narrow wavelength band for determining the proportion of water in the helium.

22. A spark spectroscopic high-pressure gas analyzer comprising:
   a spark chamber including a pair of electrodes for receiving a sample of pressurized gas to be analyzed;
   means for providing a voltage across said electrodes for generating a spark in said pressurized gas sample;
   means for detecting a first selected narrow wavelength band of the radiation emitted from the spark discharge in said pressurized gas corresponding to a component to be detected in the gas;
   means for integrating, during the afterglow time interval of the spark emission, the intensity of the emission in the first wavelength band;
   means responsive to a signal representative of the integrated intensity of the emission in the selected narrow wavelength band for determining the proportion of the component in the gas; and
   means for compensating the intensity of the emission in the first wavelength band for variations not due to variations in the proportion of the component being detected in the gas.

23. The gas analyzer of claim 22 in which said means for compensating includes means for averaging a signal repensentative of the intensity of the emission in the first band over a plurality of spark discharge cycles.

24. The gas analyzer of claim 23 in which said means for integrating and said means for averaging a signal representative of intensity of the emission in the first band include a boxcar averager.

25. The gas analyzer of claim 22 in which said means for compensating includes means for detecting the radiation emitted from the spark discharge in the pressurized gas in a second selected narrow wavelength band which does not correspond to the component to be detected in the gas, and means for combining a signal representative of the intensity of the emission in the first band with a signal representative of the intensity in the second band.

26. The gas analyzer of claim 25 in which said means for compensating further includes means for integrating, during the afterglow time interval of the spark emission, the intensity of the radiation in the second selected band.

27. The gas analyzer of claim 26 in which said means for compensating further includes first means, responsive to said means for integrating the intensity of emission in the first band, for averaging over a plurality of spark discharge cycles the integrated intensity of emission in the first band and second means, responsive to said means for integrating the intensity of emission in the second band, for averaging over a plurality of spark discharge cycles the integrated intensity of emission in the second band.

28. The gas analyzer of claim 27 in which said means for integrating the intensity and means for averaging the integrated intensity in the first selected band includes a boxcar averager.

29. The gas analyzer of claim 27 in which said means for integrating the intensity and means for averaging the integrated intensity in the second selected band includes a boxcar averager.

30. The gas analyzer of claim 27 in which said means for combining includes means, responsive to said first and second means for averaging, for comparing the averaged integrated intensity of the emitted radiation in the first band and the averaged integrated intensity of the emitted radiation in the second band and providing to said means for determining an output representative of the averaged integrated intensity of the emission in the first band.

31. The gas analyzer of claim 26 in which said means for combining includes means for comparing the integrated intensity of the emission in the first band and the integrated intensity of the emission in the second band.

32. The gas analyzer of claim 31 in which said means for combining further includes means responsive to said means for comparing for averaging over a plurality of spark discharge cycles the output from said means for comparing and providing an averaged output to said means for determining.

33. A spark spectroscopic high-pressure gas analyzer comprising:
a spark chamber including a pair of electrodes for receiving a sample of pressurized gas to be analyzed;
means for providing a voltage across said electrodes for generating a spark in said pressurized gas sample;
means for detecting a first selected narrow wavelength band of the radiation emitted from the spark discharge in said pressurized gas corresponding to a component to be detected in the gas;
means for integrating, during the afterglow time interval of the spark emission, the intensity of the emission in the first wavelength band;
means responsive to a signal representative of the integrated intensity of the emission in the selected narrow wavelength band for determining the proportion of the component in the gas; and
means for sensing the pressure of said gas to be analyzed, said means for determining being further responsive to said means for sensing the pressure for determining the proportion of the component in the gas at the sensed pressure.

34. A spark spectroscopic high-pressure gas analyzer comprising:
a spark chamber including a pair of electrodes for receiving a sample of pressurized gas to be analyzed;
means for providing a voltage across said electrodes for generating a spark in said pressurized gas sample;
means for detecting a first selected narrow wavelength band of the radiation emitted from the spark discharge in said pressurized gas coreponding to a component to be detected in the gas;
means for integrating, during the afterflow time interval of the spark emission, the intensity of the emission in the first wavelength band;
means responsive to a signal representative of the integrated intensity of the emission in the selected narrow wavelength band for determining the proportion of the component in the gas; and
means for sensing the temperature of said gas to be analyzed, said means for determining being further responsive to said means for sensing the pressure for determining the proportion of the component in the gas at the sensed temperature.

35. A spark spectroscopic high-pressure gas analyzer comprising:
a spark chamber including a pair of electrodes for receiving a sample of pressurized gas to be analyzed;
means for providing a voltage across said electrodes for generating a spark in said pressurized gas sample;
means for detecting a first selected narrow wavelength band of the radiation emitted from the spark discharge in said pressurized gas corresponding to a component to be detected in the gas;
means for integrating, during the afterglow time interval of the spark emission, the intensity of the emission in the first wavelength band; and
means responsive to a signal representative of the integrated intensity of the emission in the selected narrow wavelength band for determining the proportion of the component in the gas, said means for determining including means for retrieving a stored predetermined proportion of the component in the gas corresponding to a signal representative of the integrated intensity of the emission in the first band.

36. A spark spectroscopic high-pressure gas analyzer comprising:
a spark chamber including a pair of electrodes for receiving a sample of pressurized gas to be analyzed;
means for providing a voltage across said electrodes for generating a spark in said pressurized gas sample;
means, including monochromator means, for detecting a first selected narrow wavelength band of the radiation emitted from the spark discharge in said pressurized gas corresponding to a component to be detected in the gas;
means for integrating, during the afterglow time interval of the spark emission, the intensity of the emission in the first wavelength band; and
means responsive to a signal representative of the integrated intensity of the emission in the selected narrow wavelength band for determining the proportion of the component in the gas.

* * * * *

UNITED STATES PATENT AND TRADEMARK OFFICE
CERTIFICATE OF CORRECTION

PATENT NO. : 4,723,438

DATED : February 9, 1988

INVENTOR(S) : Adler-Golden, et al

It is certified that error appears in the above-identified patent and that said Letters Patent is hereby corrected as shown below:

Col. 1, line 5, add the following:

-- The invention was made with Governmental support under DE-AC02-83ER80084 awarded by the Department of Energy. The Government has certain rights in the invention.--

Signed and Sealed this

Seventeenth Day of December, 1991

Attest:

HARRY F. MANBECK, JR.

Attesting Officer

Commissioner of Patents and Trademarks